United States Patent
Mattar

(10) Patent No.: US 7,660,689 B2
(45) Date of Patent: Feb. 9, 2010

(54) SINGLE AND MULTIPHASE FLUID MEASUREMENTS

(75) Inventor: Wade M. Mattar, Wrentham, MA (US)

(73) Assignee: Invensys Systems, Inc., Foxboro, MA (US)

(*) Notice: Subject to any disclaimer, the term of this patent is extended or adjusted under 35 U.S.C. 154(b) by 0 days.

(21) Appl. No.: 11/745,356

(22) Filed: May 7, 2007

(65) Prior Publication Data

US 2008/0028822 A1    Feb. 7, 2008

Related U.S. Application Data

(60) Provisional application No. 60/746,744, filed on May 8, 2006.

(51) Int. Cl.
*G06F 19/00* (2006.01)
*G01F 1/84* (2006.01)

(52) U.S. Cl. .................................. 702/100; 73/861.354

(58) Field of Classification Search ................. 702/50, 702/55, 100; 73/861.27, 861.52, 861.354, 73/861.356
See application file for complete search history.

(56) References Cited

U.S. PATENT DOCUMENTS

| | | | |
|---|---|---|---|
| 4,776,222 A * | 10/1988 | Lew | 73/862.68 |
| 4,884,458 A * | 12/1989 | Lew | 73/861.24 |
| 5,029,482 A | 7/1991 | Liu et al. | |
| 5,224,372 A | 7/1993 | Kolpak | |
| 5,224,387 A | 7/1993 | Lindenbaum et al. | |
| 5,230,254 A | 7/1993 | Craft | |
| 5,259,250 A | 11/1993 | Kolpak | |
| 5,594,180 A | 1/1997 | Carpenter et al. | |
| 5,597,949 A | 1/1997 | Kalotay | |
| 6,318,156 B1 | 11/2001 | Dutton et al. | |
| 6,327,914 B1 | 12/2001 | Dutton | |
| 6,345,536 B1 | 2/2002 | Morrison et al. | |
| 7,013,715 B2 | 3/2006 | Dutton et al. | |
| 7,032,432 B2 | 4/2006 | Gysling et al. | |
| 7,096,719 B2 | 8/2006 | Gysling | |
| 7,134,320 B2 | 11/2006 | Gysling et al. | |
| 7,143,638 B1 | 12/2006 | Scott | |
| 7,152,460 B2 | 12/2006 | Gysling et al. | |
| 7,165,464 B2 | 1/2007 | Gysling et al. | |
| 7,299,705 B2 | 11/2007 | Gysling | |
| 7,328,624 B2 | 2/2008 | Gysling et al. | |
| 7,337,075 B2 | 2/2008 | Gysling et al. | |
| 7,343,818 B2 | 3/2008 | Gysling et al. | |
| 7,367,240 B2 | 5/2008 | Gysling et al. | |
| 7,380,438 B2 | 6/2008 | Gysling et al. | |
| 7,380,439 B2 | 6/2008 | Gysling et al. | |
| 7,389,687 B2 | 6/2008 | Gysling et al. | |

(Continued)

OTHER PUBLICATIONS

International Search Report and Written Opinion issued in PCT/US07/68386, dated Feb. 28, 2008.

(Continued)

*Primary Examiner*—Bryan Bui
(74) *Attorney, Agent, or Firm*—Fish & Richardson P.C.

(57) ABSTRACT

A first property of a process fluid is measured using a volumetric flowrate measuring device. A second property of the process fluid is measured using a Coriolis flowmeter. A third property of the process fluid is determined based on the measured first property and the measured second property.

20 Claims, 9 Drawing Sheets

U.S. PATENT DOCUMENTS

| | | | |
|---|---|---|---|
| 2001/0000060 A1* | 3/2001 | Toma et al. | 73/61.44 |
| 2004/0221660 A1* | 11/2004 | Dutton et al. | 73/861.354 |
| 2005/0016292 A1* | 1/2005 | Dutton et al. | 73/861.03 |
| 2005/0081643 A1* | 4/2005 | Mattar et al. | 73/861.355 |
| 2005/0193832 A1 | 9/2005 | Tombs | |
| 2006/0123923 A1* | 6/2006 | Dutton et al. | 73/861.354 |
| 2006/0161366 A1* | 7/2006 | Mattar et al. | 702/100 |
| 2007/0006744 A1 | 1/2007 | Gysling | |
| 2007/0157737 A1 | 7/2007 | Gysling et al. | |
| 2007/0186625 A1 | 8/2007 | Rogers et al. | |
| 2007/0193373 A1* | 8/2007 | Xie et al. | 73/863.03 |
| 2007/0289357 A1 | 12/2007 | Mattar et al. | |
| 2008/0034890 A1 | 2/2008 | Barua et al. | |
| 2008/0053240 A1 | 3/2008 | Henry et al. | |
| 2008/0257066 A1 | 10/2008 | Henry et al. | |
| 2008/0257067 A1 | 10/2008 | Henry et al. | |

OTHER PUBLICATIONS

U.S. Appl. No. 11/745,337, filed May 7, 2007, 28 pages.
Office Action for U.S. Appl. No. 11/745,337, mailed Jun. 4, 2008, 7 pages.
Office Action for U.S. Appl. No. 11/745,337, mailed Dec. 18, 2008.
Office Action for U.S. Appl. No. 11/745,337, mailed Jun. 8, 2009.

* cited by examiner

SINGLE AND MULTIPHASE FLUID MEASUREMENTS

CROSS-REFERENCE TO RELATED APPLICATIONS

This application claims priority to U.S. Provisional Application Ser. No. 60/746,744, titled SINGLE AND MULTIPHASE FLUID MEASUREMENTS, and filed on May 8, 2006, which is incorporated by reference.

TECHNICAL FIELD

This description relates to flowmeters.

BACKGROUND

Flowmeters provide information about materials being transferred through a conduit. For example, mass flowmeters provide a measurement of the mass of material being transferred through a conduit. Similarly, densitometers provide a measurement of the density of material flowing through a conduit. Mass flowmeters also may provide a measurement of the density of the material.

For example, Coriolis-type mass flowmeters are based on the Coriolis effect, in which material flowing through a conduit becomes a radially-travelling mass that is affected by a Coriolis force and therefore experiences an acceleration. Many Coriolis-type mass flowmeters induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

SUMMARY

Figure 1A:
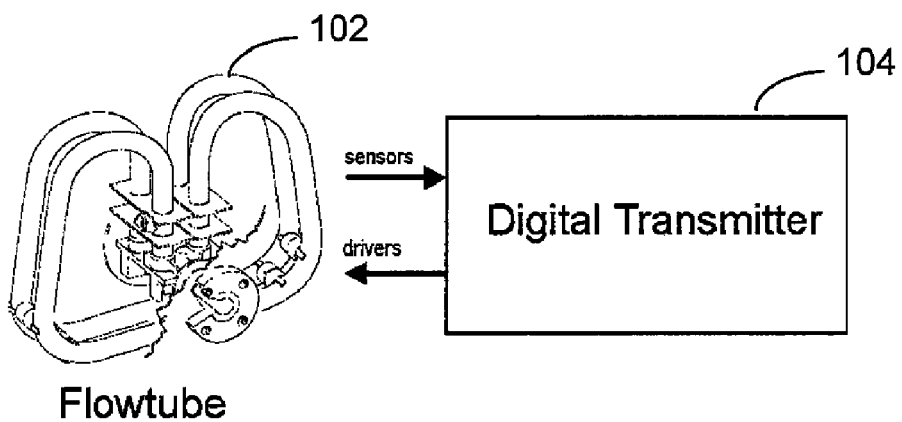
FIG. 1A is an illustration of a Coriolis flowmeter using a bent flowtube.

In one general aspect, a first property of a process fluid is measured using a volumetric flowrate measuring device. A second property of the process fluid is measured using a Coriolis flowmeter. A third property of the process fluid is determined based on the measured first property and the measured second property.

Implementations include one or more of the following features. For example, the first property may be a volumetric flowrate, the second property may be a mass flowrate, and the third property may be a bulk density. The process fluid may include a gas component and a liquid component. A mass flowrate of the gas component may be determined based on the determined bulk density. A mass flowrate of the liquid component may be determined based on the determined bulk density. The process fluid may be a wet gas. The measured mass flowrate may be corrected based on the determined bulk density. The determined bulk density may be corrected based on the corrected mass flowrate.

In another general aspect, a first property of a process fluid is measured using a differential pressure flowmeter. A second property of the process fluid is measured using a Coriolis flowmeter. A third property of the process fluid is determined based on the measured first property and the measured second property.

Implementations may include one or more of the following features. For example, the process fluid may be a wet gas. The first property may be a mass flowrate of the wet gas as a dry gas, and the second property may be a mass flowrate of the wet gas. Determining the third property of the wet gas based on the mass flow rate of the wet gas as a dry gas and the mass flow rate of the wet gas may include determining a mixture quality of the wet gas; and correcting the mass flowrate of the wet gas based on the mixture quality. Determining the third property of the wet gas based on the mass flow rate of the wet gas as a dry gas and the mass flow rate of the wet gas may include refining the determined mixture quality based on the corrected mass flowrate. The third property may be a mass flowrate of a liquid component of the wet gas. The third property may be a mass flowrate of a gas component of the wet gas. The differential pressure flowmeter may include an orifice plate flowmeter.

Implementations of any of the techniques described above may include a method or process, a system, a flowmeter, or instructions stored on a storage device of a flow meter transmitter. Details of particular implementations are set forth in the accompanying drawings and description below. Other features will be apparent from the following description, including the drawings, and the claims.

DETAILED DESCRIPTION

Types of flowmeters include digital Coriolis flowmeters. For example, U.S. Pat. No. 6,311,136, which is hereby incorporated by reference, discloses the use of a digital Coriolis flowmeter and related technology including signal processing and measurement techniques. Such digital flowmeters may be very precise in their measurements, with little or negligible noise, and may be capable of enabling a wide range of positive and negative gains at the driver circuitry for driving the conduit. Such digital Coriolis flowmeters are thus advantageous in a variety of settings. For example, commonly-assigned U.S. Pat. No. 6,505,519, which is incorporated by reference, discloses the use of a wide gain range, and/or the use of negative gain, to prevent stalling and to more accurately exercise control of the flowtube, even during difficult conditions such as two-phase flow (e.g., a flow containing a mixture of liquid and gas).

Although digital Coriolis flowmeters are specifically discussed below with respect to, for example, FIGS. 1A, 1B and 2, it should be understood that analog Coriolis flowmeters also exist. Although such analog Coriolis flowmeters may be prone to typical shortcomings of analog circuitry, e.g., low precision and high noise measurements relative to digital Coriolis flowmeters, they also may be compatible with the various techniques and implementations discussed herein. Thus, in the following discussion, the term "Coriolis flowmeter" or "Coriolis meter" is used to refer to any type of device and/or system in which the Coriolis effect is used to measure a mass flow, density, and/or other parameters of a material(s) moving through a flowtube or other conduit.

FIG. 1A is an illustration of a digital Coriolis flowmeter using a bent flowtube 102. Specifically, the bent flowtube 102 may be used to measure one or more physical characteristics of, for example, a (travelling or non-travelling) fluid, as referred to above. In FIG. 1A, a digital transmitter 104 exchanges sensor and drive signals with the bent flowtube 102, so as to both sense an oscillation of the bent flowtube 102, and to drive the oscillation of the bent flowtube 102 accordingly. By quickly and accurately determining the sensor and drive signals, the digital transmitter 104, as referred to above, may provide for fast and accurate operation of the bent flowtube 102. Examples of the digital transmitter 104 being used with a bent flowtube are provided in, for example, commonly-assigned U.S. Pat. No. 6,311,136.

Figure 1B:
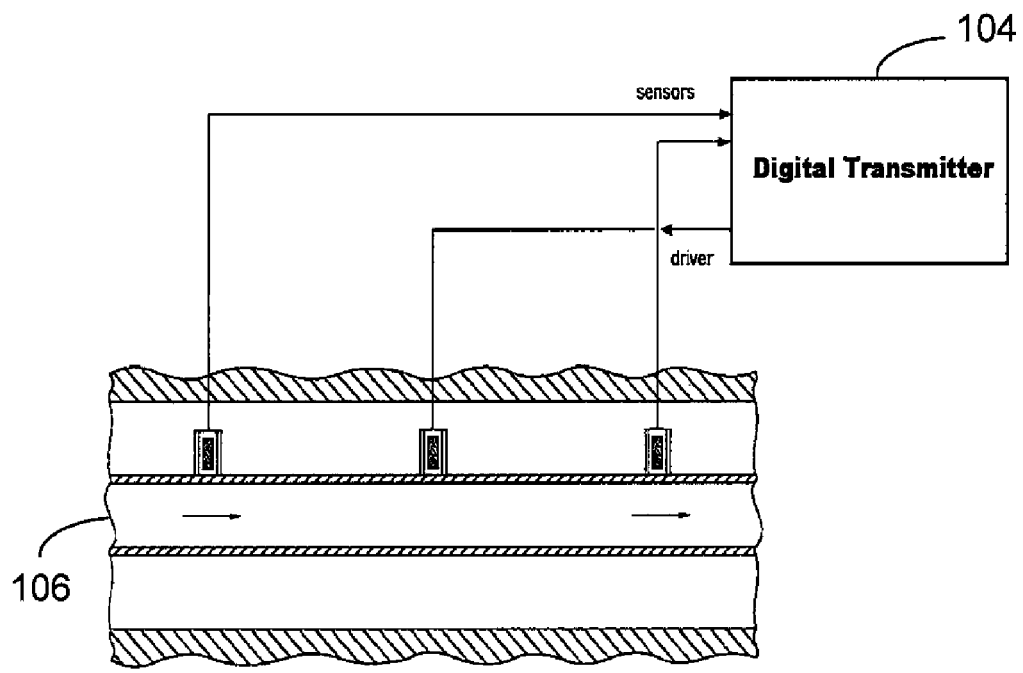
FIG. 1B is an illustration of a Coriolis flowmeter using a straight flowtube.

FIG. 1B is an illustration of a digital Coriolis flowmeter using a straight flowtube 106. More specifically, in FIG. 1B, the straight flowtube 106 interacts with the digital transmitter 104. Such a straight flowtube operates similarly to the bent flowtube 102 on a conceptual level, and has various advantages/disadvantages relative to the bent flowtube 102. For example, the straight flowtube 106 may be easier to (completely) fill and empty than the bent flowtube 102, simply due to the geometry of its construction. In operation, the bent flowtube 102 may operate at a frequency of, for example, 50-110 Hz, while the straight flowtube 106 may operate at a frequency of, for example, 300-1,000 Hz. The bent flowtube 102 represents flowtubes having a variety of diameters, and may be operated in multiple orientations, such as, for example, in a vertical or horizontal orientation.

Figure 2:
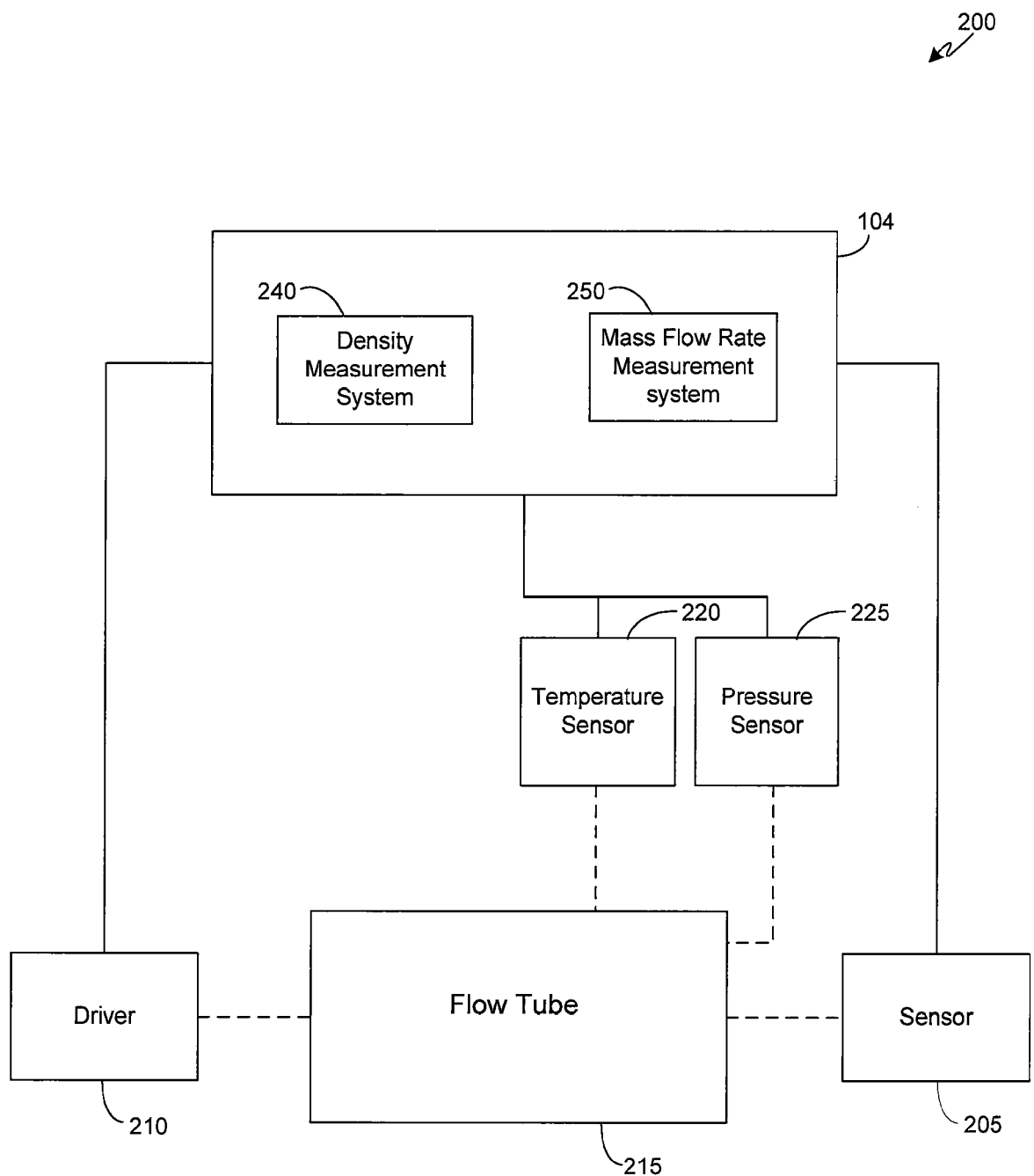
FIG. 2 is a block diagram of a Coriolis flowmeter.

Referring to FIG. 2, a digital mass flowmeter 200 includes the digital transmitter 104, one or more motion sensors 205, one or more drivers 210, a flowtube 215 (which also may be referred to as a conduit, and which may represent either the bent flowtube 102, the straight flowtube 106, or some other type of flowtube), a temperature sensor 220, and a pressure sensor 225. The digital transmitter 104 may be implemented using one or more of, for example, a processor, a Digital Signal Processor (DSP), a field-programmable gate array (FPGA), an ASIC, other programmable logic or gate arrays, or programmable logic with a processor core. It should be understood that, as described in U.S. Pat. No. 6,311,136, associated digital-to-analog converters may be included for operation of the drivers 210, while analog-to-digital converters may be used to convert sensor signals from the sensors 205 for use by the digital transmitter 104.

The digital transmitter 104 may include a (bulk) density measurement system 240 and a mass flowrate measurement system 250. Density measurement system 240 and mass flowrate measurement system 250 may generate measurements of, respectively, density and/or mass flowrate of a material flowing through the flowtube 215 based at least on signals received from the motion sensors 205. The digital transmitter 104 also controls the drivers 210 to induce motion in the flowtube 215. This motion is sensed by the motion sensors 205.

Density measurements of the material flowing through the flowtube are related to, for example, the frequency of the motion of the flowtube 215 that is induced in the flowtube 215 (typically the resonant frequency) by a driving force supplied by the drivers 210, and/or to the temperature of the flowtube 215. Similarly, mass flow through the flowtube 215 is related to the phase and frequency of the motion of the flowtube 215, as well as to the temperature of the flowtube 215.

The temperature in the flowtube 215, which is measured using the temperature sensor 220, affects certain properties of the flowtube, such as its stiffness and dimensions. The digital transmitter 104 may compensate for these temperature effects. Also in FIG. 2, a pressure sensor 225 is in communication with the transmitter 104, and is connected to the flowtube 215 so as to be operable to sense a pressure of a material flowing through the flowtube 215.

It should be understood that both the pressure of the fluid entering the flowtube 215 and the pressure drop across relevant points on the flowtube may be indicators of certain flow conditions. Also, while external temperature sensors may be used to measure the fluid temperature, such sensors may be used in addition to an internal flowmeter sensor designed to measure a representative temperature for flowtube calibrations. Also, some flowtubes use multiple temperature sensors for the purpose of correcting measurements for an effect of differential temperature between the process fluid and the environment (e.g., a case temperature of a housing of the flowtube).

In FIG. 2, it should be understood that the various components of the digital transmitter 104 are in communication with one another, although communication links are not explicitly illustrated, for the sake of clarity. Further, it should be understood that conventional components of the digital transmitter 104 are not illustrated in FIG. 2, but are assumed to exist within, or be accessible to, the digital transmitter 104. For example, the digital transmitter 104 will typically include drive circuitry for driving the driver 210, and measurement circuitry to measure the oscillation frequency of the flowtube 215 based on sensor signals from sensors 205 and to measure the phase between the sensor signals from sensors 205.

Under certain conditions, a Coriolis flowmeter can, by means of the resonant frequency of vibration of the flowtube, accurately determine the bulk density of a process fluid in the flowtube 215. That is, an accurate bulk density of the process fluid can be determined under certain conditions.

Also, in some situations, the process fluid may contain more than one phase by being a mixture of two or more materials (for example, oil and water or a fluid with entrained gas), by being the same material in different phases (for example, liquid water and water vapor), or by being different materials in different phases (for example, water vapor and oil). In some multi-phase flow conditions, a Coriolis flowmeter, either alone or in combination with other equipment, may accurately determine the density and mass flowrate of the constituent phases.

Under other conditions, however, a Coriolis flowmeter may not perform in a satisfactory manner. For instance, under some conditions, a Coriolis flowmeter may not be able to measure the bulk density, the density of constituent components of a multi-phase flow, or the mass flowrates of constituent components of a multi-phase flow within the required tolerances needed in a particular application. In other words, the Coriolis flowmeter may not be able to measure such items within the requisite degree of accuracy for a given use of the Coriolis flowmeter.

Examples of such conditions include situations in which the process fluid is a single-phase gas, and when the process fluid is a wet-gas (that is, it contains mostly a gas component, but has some liquid component). A wet gas typically occurs in applications involving natural gas, where the gas component is the natural gas, and the liquid component may be water, hydrocarbons, or compressor oil. In natural gas applications, it may be desirable to accurately measure the density of the process fluid in order to calculate the energy flow of the process fluid. Other applications in which a wet gas occurs may include applications involving steam as the process fluid.

A wet gas generally includes a process fluid that contains 5% by volume or less of a liquid or, in other words, a process fluid that has a void fraction of 0.95 (95%) or more. However, the techniques described below with respect to wet gasses are not limited to process fluids that contain 5% by volume of less of a liquid. Rather, the techniques are bounded by the required accuracy of a given application, with the accuracy depending on the accuracy of the Coriolis flowmeter and other meters described below for a given void fraction.

Figure 3A:
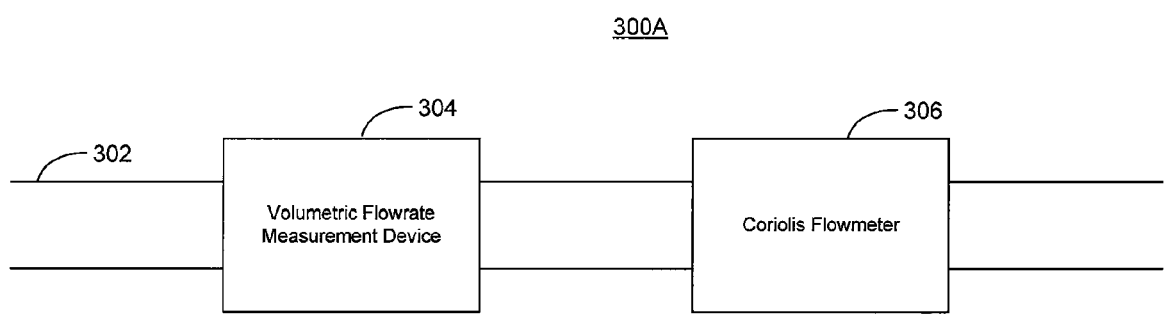
FIG. 3A is a block diagram showing a system that includes a volumetric flowrate measuring device and a Coriolis flowmeter.

Referring to FIG. 3A, a system 300A may be used to accurately measure the bulk density of a process fluid under conditions in which a Coriolis flowmeter does not measure the bulk density with the required accuracy. In addition, system 300A may be used to accurately measure the bulk density of a wet gas or other multi-phase process fluid, and the mass flowrates of the constituent components of such a multi-phase process fluid.

System 300A includes a conduit 302 that carries the process fluid, a volumetric flowrate measurement device 304 that measures the (bulk) volumetric flowrate of the process fluid, and a Coriolis flowmeter 306 that measures the (bulk) mass flowrate of the process fluid.

In one implementation, the volumetric flowrate measuring device 304 is a vortex shedding flowmeter. Generally, a vortex shedding flowmeter may measure the volumetric flowrate of a single phase gas and a wet gas (and possibly other multi-phase fluids) with a reasonable degree of accuracy. Other volumetric flowrate measuring devices may be used, depending on the accuracy required in a given application.

In general, the vortex flowmeter 304 has an output that is proportional to the average velocity of the process fluid. If the cross sectional area of the conduit 302 is fixed or known proportional to volumetric flowrate, then:

$$S_V = K_V \times A_{pipe} \times \overline{V} = K_V Q_V$$

where $S_V$=volumetric signal from the meter
$K_V$=proportionality constant
$A_{pipe}$=area of pipe
$Q_V$=volumetric flowrate at the vortex meter The Coriolis mass flowmeter 306 generally has the following output for single phase:

$$S_M = K_M \times \dot{M}$$

where $S_M$=mass signal from the meter
$K_M$=proportionality constant
$\dot{M}$=mass flowrate at the Coriolis meter Also, the mass flowrate at the vortex meter 304 is the same as the Coriolis meter 306 due to conservation of mass. Therefore:

$$\dot{M} = S_M / K_M \ \& \ Q_V = S_V / K_V \ \& \ \dot{M} = \rho_{fluid} \times Q_V$$

finally $$\rho_{fluid} = \dot{M} / Q_V$$

where $\dot{M}$ is the mass flowrate at the Coriolis meter, $Q_V$ is the volumetric flowrate at the vortex meter, and $\rho_{fluid}$ is fluid density at the vortex meter.

After obtaining the density of the process fluid at the vortex meter 304, the density at other points along the conduit 302 can be calculated by ratiometrically compensating for temperature and pressure (and compressibility for higher accuracy) for changes in location along the conduit 302. For example, the temperature and pressure at the vortex meter 304 can be measured, along with the temperature and pressure at the desired location of the conduit. Then, using the ideal gas law or the real gas law, the density of the gas can be calculated at the desired location of the conduit 302.

The above calculation of the density at the vortex meter 304 may be performed for a single phase gas and a wet gas (or some other multi-phase fluid). In the case of a wet gas (or other multi-phase fluid), this density may be used to calculate the mass flowrate of the constituent components of the process fluid. In this case, the knowledge of the gas and liquid densities may be required.

In general, it has been shown for a vortex meter at reasonably high void fraction of 0.8 or more the vortex meter will still give a reasonably accurate indication of volumetric flowrate since the liquid will tend to travel as a mist within the gas provided the gas flowrate is high enough. The actual bounds depend on the accuracy required. Assuming that the Coriolis flowmeter 306 is producing no error due to liquid loading, then the above equation yields:

$$\rho_{bulk} = \dot{M}/Q_V$$

where $\rho_{bulk}$ is now the bulk fluid density at the vortex meter.

The density of the gas component may be determined through pressure and temperature measurements at the vortex meter 304 combined with the ideal gas law or real gas law or some other equation of state for the gas. The liquid density may be determined through sampling or may be approximated given knowledge about the makeup of the liquid. Again how accurate this needs to be depends on how accurate the end result needs to be. In many applications involving wet gas, for example, accuracies of 5% may be sufficient.

Knowing the densities of the liquid and the gas components yields:

$$GVF = \frac{\rho_{bulk} - \rho_{liquid}}{\rho_{gas} - \rho_{liquid}}$$

Volumetric flowrate of the gas then equals $$Q_{gas} = GVF \times Q_V$$

And for the liquid $$Q_{liquid} = (1 - GVF) \times Q_V.$$

The mass flowrates or the gas and liquid components can be calculated by multiplying $Q_{gas}$ and $Q_{liquid}$ by the gas and liquid densities, respectively.

When a Coriolis flowmeter is used to measure the mass flowrate of a multi-phase fluid, such as wet gas, there may be errors in the mass flowrate measurement due to liquid loading. In other words, damping caused by the multi-phase fluid may result in errors in the measured mass flowrate. Techniques, such as those described in U.S. Pat. No. 6,505,519 may be used to correct the mass flowrate measurements in such situations. However, such techniques generally employ a corrected density measurement that is performed by the Coriolis meter. In the case of a wet gas, however, the density measurement may not be accurate enough, even if it is corrected. Thus, in some implementations, the bulk density measurement from the combination of the volumetric flowrate measurement device 304 and Coriolis flowmeter 306 may be used to correct the mass flowrate measurement of the Coriolis flowmeter 306. In addition, an iterative procedure may then be used to refine the bulk density using a corrected mass flowrate from the Coriolis flowmeter 306. In other words, the bulk density measured based on system 300A may be used to correct the mass flowrate measurement of the Coriolis meter 306. The corrected mass flowrate may then be used to refine the measurement of the bulk density. The refined bulk density may then be used to refine the mass flowrate. Such an iterative process may continue until it reaches a convergence.

Figure 3B:
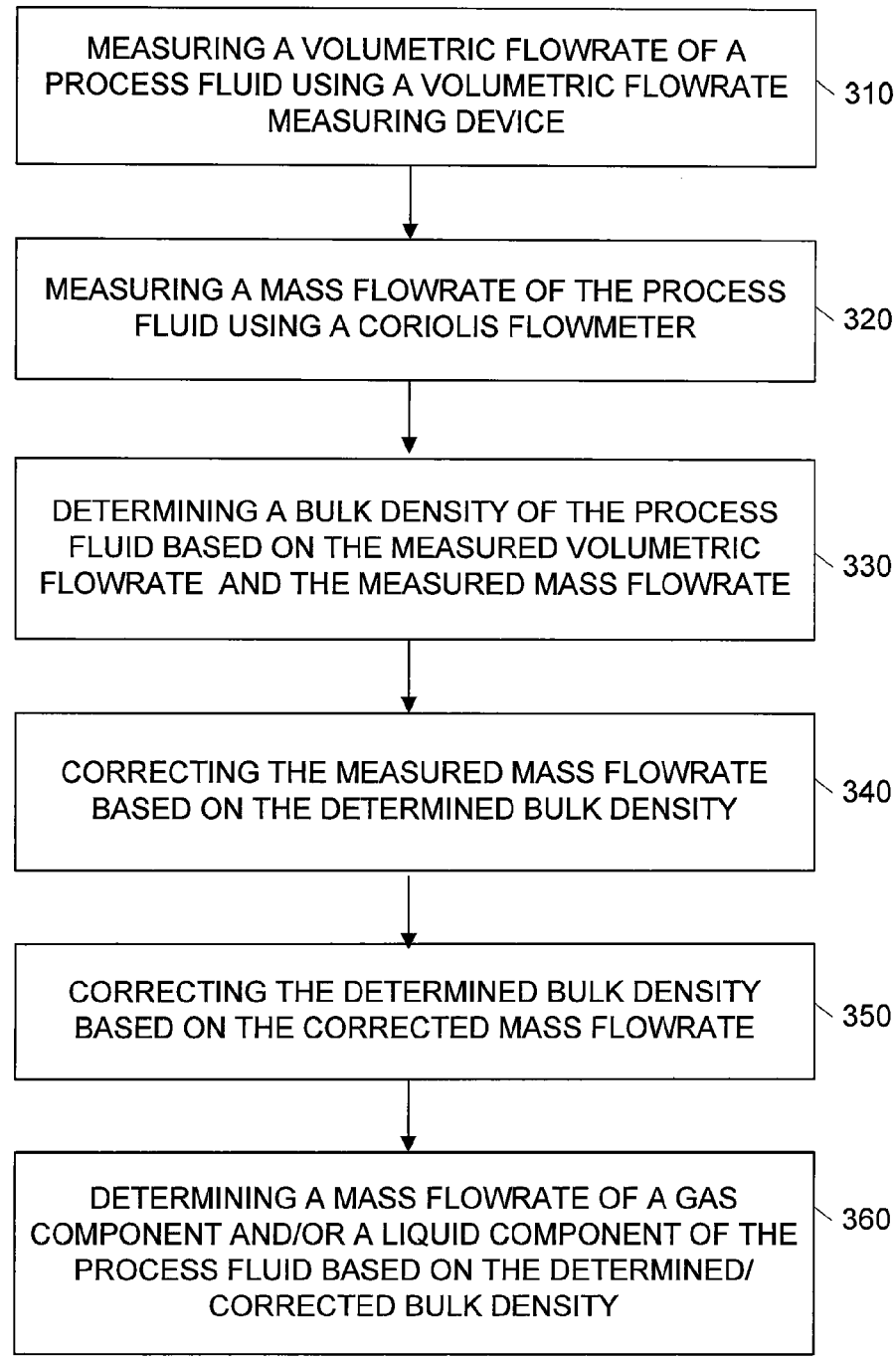
FIG. 3B is a flow chart illustrating a process for using a volumetric flowrate measuring device and a Coriolis flowmeter.

Referring to FIG. 3B, a process 300B may be used to perform the operations discussed above with respect to FIG. 3. The process 300B may be performed by the system 300A. The process 300B begins when a volumetric flowrate of a process fluid is measured using a volumetric flowrate measuring device (310). The process fluid may be a wet gas or other multi-phase process fluid. The flowrate measuring device may be, for example, the volumetric flowrate measurement device 304 discussed above. The process 300B also includes measuring a mass flowrate of the process fluid using a Coriolis flowmeter (320). The Coriolis flowmeter may be the Coriolis flowmeter 306 discussed above.

The process 300B continues when a bulk density of the process fluid is determined based on the measured volumetric flowrate and the measured mass flowrate (330). The measured mass flowrate may be corrected based on the determined bulk density (340). The determined bulk density may then be corrected based on the corrected mass flowrate (350). Operations 340 and 350 may be repeated until a convergence is reached or until a required degree of accuracy is met. Thus, the iterative process described above may be implemented by the process 300B; however, in some implementations such an iterative process may not be performed.

The process fluid may include more than one phase of fluid. For example, the process fluid may be, e.g., a wet gas that includes a gas component and a liquid component. The process 300B also may include determining a mass flowrate of the gas component and/or the liquid component of the process fluid based on the determined or corrected bulk density (360). In other words, the mass flow rate of either or both of the gas component and the liquid component may be determined from the corrected bulk density (e.g., corrected through the iterative process described above). In other implementations, the mass flow rate of these components may be derived from the determined bulk density (e.g., the bulk density determined based on the measured volumetric flowrate and the measured mass flowrate in (330)).

Figure 4:
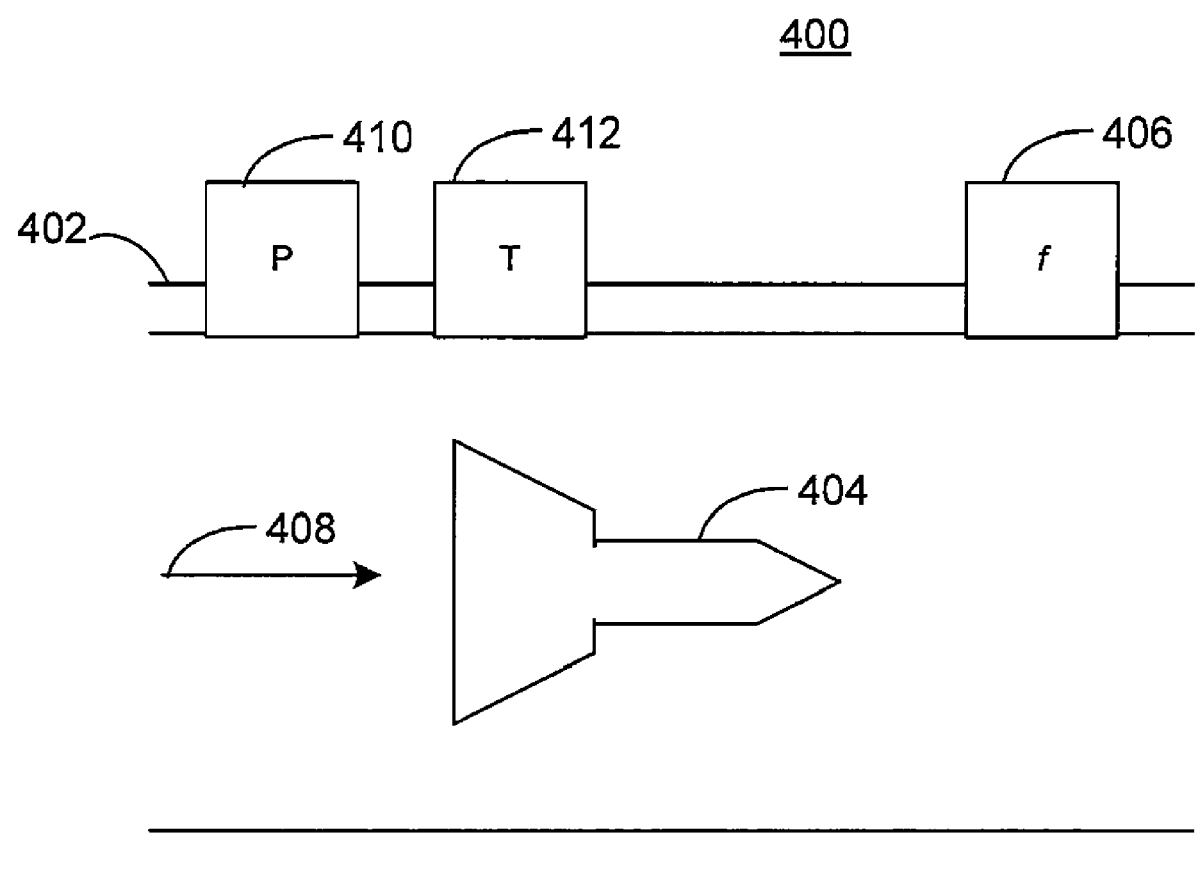
FIG. 4 is an illustration showing a vortex shedding flowmeter.

Referring to FIG. 4, vortex shedding flowmeter 400 includes a conduit 402 for carrying the process fluid. Conduit 402 contains a bluff body 404 that induces vortex shedding in a fluid flowing in the conduit 402. An arrow 408 indicates the direction of flow. A pressure sensor 406 is located downstream of the bluff body 404. The pressure sensor 406 may include, for example, a differential pressure sensor or an absolute pressure sensor, and may include materials such as, for example, a piezoelectric material. Thus, one example of the pressure sensor 406 is a piezoelectric differential pressure sensor that measures the differential pressure across the conduit 402.

In general, a vortex shedding flowmeter measures volumetric flow based on the principle of vortex shedding. Vortex shedding refers to a natural process in which a fluid passing a bluff body causes a boundary layer of slowly moving fluid to be formed along the surface of the bluff body. A low pressure area is created behind the bluff body and causes the boundary layer to roll up, which generates vortices in succession on opposite sides of the bluff body. The vortices induce pressure variations that may be sensed by the pressure sensor 406. The vortex-shedding pressure variations have a frequency that is related to the volumetric flowrate. Accordingly, by measuring the frequency of the pressure variations using the pressure sensor 406, the volumetric flowrate may be determined.

Vortex flowmeter 400 also may include pressure sensor 410 and temperature sensor 412, which may be used to calculate the density of the process fluid at other points along the conduit 302, as described above.

Figure 5:
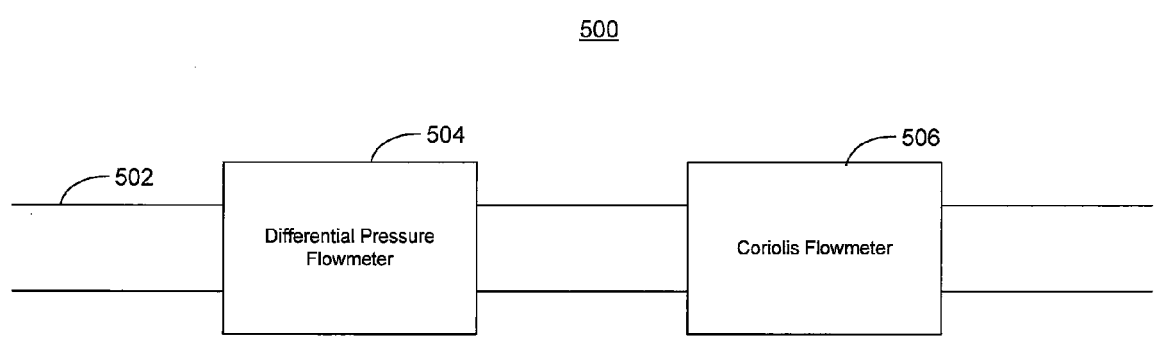
FIG. 5 is a block diagram showing a system that includes a differential pressure flowmeter and a Coriolis flowmeter.

Referring to FIG. 5, differential pressure flowmeters may be used in combination with a Coriolis meter to measure the mass flowrates of the constituent components of a wet gas or other multi-phase process fluid. As illustrated, a system 500 includes a conduit 502 that carries the process fluid (e.g., wet gas), a differential pressure flowmeter 504 that measures the mass flowrate of the process fluid as if it was a single phase. For example, in the case of wet gas, the differential pressure flowmeter measures the mass flowrate of the process fluid as if it was a dry gas (i.e., a single phase gas). The system 500 also includes a Coriolis flowmeter 506 that measures the (bulk) mass flowrate of the process fluid. The mass flowrate measured by the differential pressure flowmeter 504 and the mass flowrate measured by the Coriolis meter 506 are then used to calculate the mass flowrates of the gas component and the liquid component.

Figure 6:
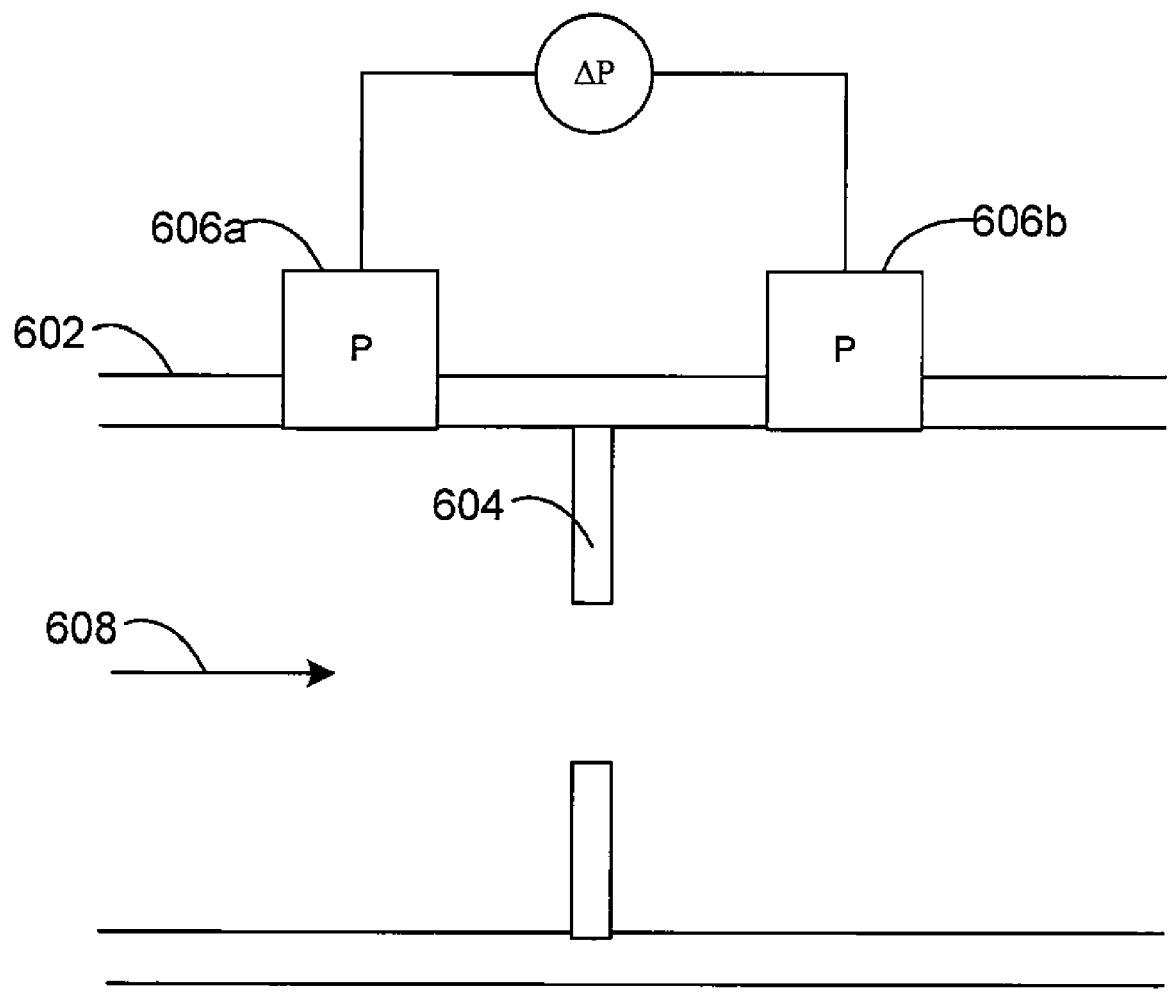
FIG. 6 is an illustration showing an orifice plate flowmeter.

Referring to FIG. 6, an explanation for determining the mass flowrate of constituent components of a wet gas using system 500 is described with respect to an implementation using an orifice plate flowmeter 600. In general, differential pressure flowmeters guide the flow of process fluid into a section with a cross sectional area different than the conduit carrying the fluid. This results in variations of the flow velocity and the pressure. By measuring the changes in pressure, the flow velocity can then be calculated. The mass flowrate can then be calculated from the flow velocity.

In particular, an orifice plate (e.g., the orifice plate 604) is typically a flat plate with an orifice located in the plate. An orifice plate is normally mounted between a pair of flanges and is installed in a straight run of smooth pipe to avoid disturbance of flow patterns from fittings and valves.

Flow through an orifice plate is characterized by a change in velocity. As the fluid passes through the orifice, the fluid converges, and the velocity of the fluid increases to a maximum value. At this point, the pressure is at a minimum value. As the fluid diverges to fill the entire pipe area, the velocity decreases back to the original value. The pressure increases to about 60% to 80% of the original input value. The pressures on both sides of the orifice are measured, resulting in a differential pressure, which is proportional to the flow velocity. From the flowrate, the mass flowrate can be calculated.

Thus, the orifice plate flowmeter 600 includes a conduit 602 for carrying the process fluid and an orifice plate 604 located in the conduit 602. An arrow 608 illustrates the direction of flow. Upstream from the orifice plate 604 is a first pressure sensor 606a and downstream from the orifice plate 604 is a second pressure sensor 606b. The difference between the measurements of the first sensor 606a and the second sensor 606b provides the differential pressure, which may be used to calculate the flow velocity and the mass flowrate.

In general, once the orifice plate flowmeter 600 is used to determine the differential pressure, the differential pressure can be used to calculate the mass flowrate of the process fluid as if the process fluid was a dry gas instead of a wet gas. This can be used with a bulk mass flowrate measurement of the Coriolis meter 506 to calculate the mass flowrates of the liquid and gas components of the wet gas.

The following is an explanation of how to calculate the mass flowrates of these components. For an orifice plate with a dry gas, known equations may be used to derive the mass flowrate from the differential pressure $\Delta P$:

$$\dot{M}_{gas,dry} = f(\Delta P, P_1, \rho_{1gas}, C_{gas}, Y_1)$$

where $\Delta P$=diff pressure across plate
$P_1$=pressure upstream of plate
$\rho_{1gas}$=density of dry gas upstream
$C_{gas}$=discharge coefficient
$Y_1$=gas expansion factor Murdock's equations, discussed, for example, in Flow Measurement Engineering Handbook, R. W. Miller, McGraw Hill, 3rd edition, describe a correction factor used to correct measurements of the mass flowrate when a wet gas is present instead of a dry gas. Based on Murdock's equations, which are valid up to about 90% gas by mass, the above equation for the mass flowrate becomes:

$$\dot{M}_{gas,wet} = \dot{M}_{gas,dry} \cdot \left[ \frac{1}{X + 1.26 \cdot (1-X) \cdot \sqrt{\rho_{1gas}/\rho_{liq}}} \right]$$

where $$X = \frac{\text{mass of gas}}{\text{mass of liquid} + \text{mass of gas}}$$

$\rho_{liq}$ = liquid density

Assuming that the densities of the two components are known, the only unknown to the right of the above equation is X, which is the mixture quality of the process fluid based on the mass of the gas and the mass of the liquid.

Using the Coriolis flowmeter 506, a measurement of the mass flowrate of the mixture, $M_{cor}$, can be obtained. Because of conservation of mass, this mass flowrate is equivalent to $M_{gas,wet}$ at the orifice plate flowmeter 600. Consequently:

$$\dot{M}_{Cor} = \dot{M}_{gas,dry} \cdot \left[ \frac{1}{X + 1.26 \cdot (1-X) \cdot \sqrt{\rho_{1gas}/\rho_{liq}}} \right]$$

Rearranging and solving for X:

$$X = \frac{\dot{M}_{gas,dry}/\dot{M}_{Cor} - 1.26\sqrt{\rho_{1gas}/\rho_{liq}}}{1 - 1.26\sqrt{\rho_{1gas}/\rho_{liq}}}$$

And, $$\dot{M}_{gas,true} = {}^X \dot{M}_{Cor}$$

and $$\dot{M}_{liquid} = {}^{(1-X)} \dot{M}_{Cor}$$

Thus, by measuring the differential pressure created by the orifice plate 604, the mass flowrate of the process fluid as a dry gas, $M_{gas, dry}$, can be calculated based on known equations. This mass flowrate can then be used with the bulk mass flowrate measured by the Coriolis meter 506. Both of these mass flowrates can then be used to calculate the mass flowrates of the liquid and gas components or the wet gas using any combination of the equations above for X and $M_{gas,true}$ and $M_{liquid}$.

Similar to the procedure described above, some implementations may use an iterative procedure to refine the measurement of $M_{cor}$ and calculation of X. For example, in some implementations, the initial calculation of X may be used to correct the mass flowrate measurement $M_{cor}$ of the Coriolis flowmeter 506. An iterative procedure may then be used to refine the calculation of X using a corrected mass flowrate from the Coriolis flowmeter 506, and the process may continue until it reaches a convergence.

While a particular implementation has been described using an orifice plate flowmeter 600, the Murdock correction works for other differential pressure flowmeters, such as venturi tubes and nozzles. Therefore, other implementations may use other differential pressure flowmeters. Accordingly, in general, the appropriate equation to calculate $M_{gas, dry}$ may be used for the particular differential pressure flowmeter used, and $M_{gas, dry}$ may be combined with the mass flowrate measured by the Coriolis flowmeter to calculate the mass flowrates of the gas and liquid components of the process fluid, as described above. Furthermore, other similar but different corrections that may be or have been developed to deal with wet gases may be used instead of Murdock's equations.

Figure 7A:
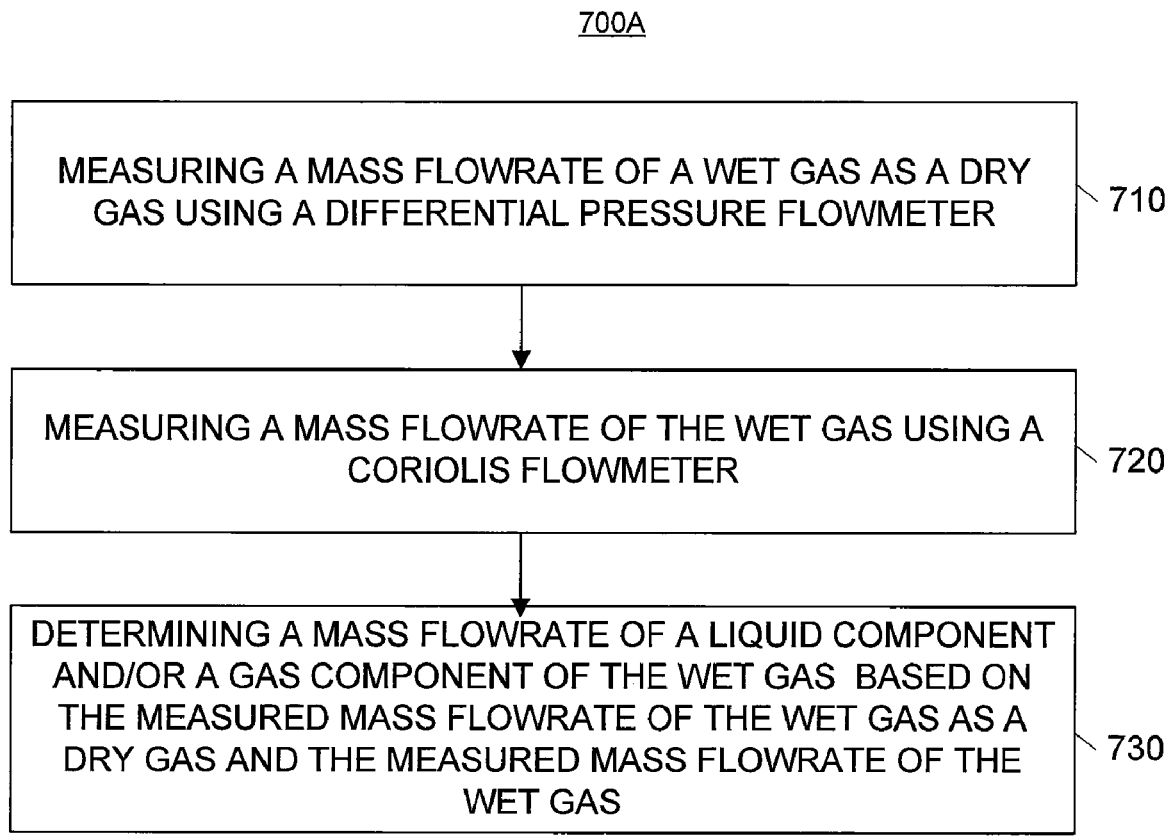
FIGS. 7A and 7B are flowcharts illustrating processes for using a differential pressure flowmeter and a Coriolis flowmeter.

Referring to FIG. 7A, a process 700 may be used to perform the operations described above. The process 700A may be performed by the system 500. Process 700A uses wet gas as an example of the process fluid, but the process 700A may be applied to other multi-phase fluids that include a liquid and gas components.

The process 700A begins when a mass flowrate of wet gas as a dry gas is measured using a differential pressure flowmeter (710). For example, the differential pressure flowmeter may be the differential pressure flowmeter 504. In another example, the differential pressure flowmeter may be the orifice plate flowmeter 600. The process 700 continues when a mass flowrate of the wet gas is measured using a Coriolis flowmeter (720). The Coriolis meter may be the Coriolis flowmeter 506 described above. The process 700A also includes determining a mass flowrate of a liquid component and/or a gas component of the wet gas based on the measured mass flowrate of the wet gas as a dry gas and the measured mass flowrate of the wet gas (730).

Figure 7B:
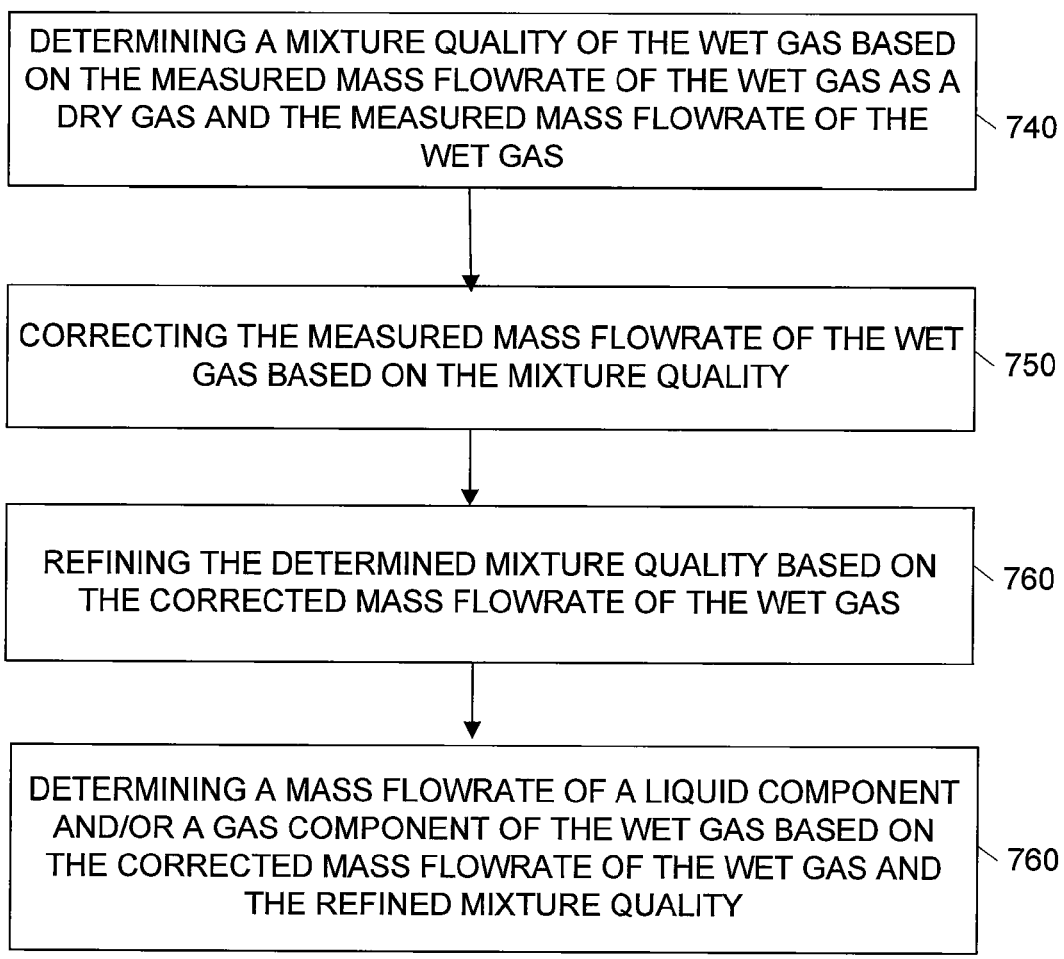

Referring to FIG. 7B, a process 700B may be performed to determine the mass flowrate of the liquid and/or gas component (730) of the wet gas (or other multi-phase fluid). Process 700B includes determining a mixture quality of the wet gas based on the measured mass flowrate of the wet gas as a dry gas and the measured mass flowrate of the wet gas (740). The mixture quality may be the mixture quality, X, which is based on the mass of the gas and the mass of the liquid included in the process fluid. The measured mass flowrate of the wet gas may be corrected based on the determined mixture quality (750). The mixture quality then may be refined based on the corrected mass flowrate of the wet gas (760). Operations 750 and 760 may be repeated until a convergence is reached or until a required degree of accuracy is met. Thus, in some implementations, the process 700B may implement the iterative process described above with respect to FIG. 6. The process 700B also includes determining a mass flowrate of a liquid component and/or a gas component of the wet gas based on the corrected mass flowrate of the wet gas and the refined mixture quality (760).

The calculations described in the various implementations may be performed by the transmitter of the Coriolis flowmeter, by a computing device coupled to the volumetric flowrate measuring device or the differential pressure flowmeter, or by a flow computer or computing device coupled to the Coriolis flowmeter and the volumetric flowrate measuring device or the differential pressure flowmeter.

A number of implementations have been described. Nevertheless, it will be understood that various modifications may be made. Accordingly, other implementations are within the scope of the following claims.

What is claimed is:

1. A method comprising:
   passing a multi-phase process fluid through a volumetric flowrate measuring device, the multi-phase process fluid including at least a first phase and a second phase;
   measuring a flowrate of the multi-phase process fluid using the volumetric flowrate measuring device;
   passing the multi-phase process fluid through a Coriolis flowmeter that is separate from the volumetric flowrate measuring device;
   measuring a property of the multi-phase process fluid using the Coriolis flowmeter; and
   determining, using one or more processing devices, a bulk density of the multi-phase process fluid based on the flowrate measured using the volumetric flowrate measuring device and the property measured using the Coriolis flowmeter.

2. The method of claim 1 wherein the flowrate comprises a volumetric flowrate and the property comprises a mass flowrate.

3. The method of claim 2 wherein the first phase of the multi-phase process fluid is a gas component and the second phase of the multi-phase process fluid is a liquid component.

4. The method of claim 3 further comprising determining a mass flowrate of the gas component based on the determined bulk density.

5. The method of claim 3 further comprising determining a mass flowrate of the liquid component based on the determined bulk density.

6. The method of claim 3 wherein the multi-phase process fluid comprises a wet gas.

7. The method of claim 2 further comprising correcting the measured mass flowrate based on the determined bulk density.

8. The method of claim 7 further comprising correcting the determined bulk density based on the corrected mass flowrate.

9. A system comprising:
   a volumetric flowrate measuring device configured to measure a flowrate of a multi-phase process fluid passing through the volumetric flowrate measuring device, the multi-phase process fluid including at least a first phase and a second phase;
   a Coriolis flowmeter that is separate from the volumetric flowrate measuring device and is configured to measure a property of the multi-phase process fluid passing through the Coriolis flowmeter; and
   a computing device configured to determine a bulk density of the process fluid based on the flowrate measured using the volumetric flowrate measuring device and the property measured using the Coriolis flowmeter.

10. The system of claim 9 wherein the flowrate comprises a volumetric flowrate and the property comprises a mass flowrate.

11. The system of claim 10 wherein the first phase of the multi-phase process fluid is a gas component and the second phase of the multi-phase process fluid is a liquid component.

12. The system of claim 11 wherein the computing device is configured to determine a mass flowrate of the gas component based on the determined bulk density.

13. The system of claim 11 wherein the computing device is configured to determine a mass flowrate of the liquid component based on the determined bulk density.

14. The system of claim 11 wherein the multi-phase process fluid comprises a wet gas.

15. The system of claim 10 wherein the computing device is configured to correct the measured mass flowrate based on the determined bulk density.

16. The system of claim 15 wherein the computing device is configured to determine bulk density based on the corrected mass flowrate.

17. The method of claim 1 wherein measuring a flowrate of a multi-phase process fluid using a volumetric flowrate measuring device comprises measuring the flowrate of the multi-phase process fluid using a vortex shedding flowmeter.

18. The system of claim 9 wherein the volumetric flowrate measuring device comprises a vortex shedding flowmeter.

19. The system of claim 9 further comprising a conduit coupled to the volumetric flowrate measuring device and the Coriolis flowmeter, the conduit configured to carry the multi-phase process fluid.

20. The system of claim 9 wherein the volumetric flowrate measuring device comprises a pressure sensor and a temperature sensor.

* * * * *